(12) United States Patent
Aebi et al.

(10) Patent No.: US 7,473,276 B2
(45) Date of Patent: Jan. 6, 2009

(54) INTERVERTEBRAL IMPLANT WITH JOINT PARTS MOUNTED ON ROLLER BODIES

(75) Inventors: Max Aebi, Bern (CH); Dominique Burkard, Gretzenbach (CH); Robert Frigg, Bettlach (CH); Beat Lechmann, Bettlach (CH); Robert Mathys, Jr., Bettlach (CH); Paul Pavlov, Nijmegen (NL)

(73) Assignee: Synthes (U.S.A.), West Chester, PA (US)

( * ) Notice: Subject to any disclaimer, the term of this patent is extended or adjusted under 35 U.S.C. 154(b) by 0 days.

(21) Appl. No.: 10/539,659

(22) PCT Filed: Dec. 17, 2002

(86) PCT No.: PCT/CH02/00704

§ 371 (c)(1),
(2), (4) Date: Jan. 17, 2007

(87) PCT Pub. No.: WO2004/054475

PCT Pub. Date: Jul. 1, 2004

(65) Prior Publication Data

US 2007/0135919 A1    Jun. 14, 2007

(51) Int. Cl.
*A61F 2/44* (2006.01)
(52) U.S. Cl. ............. 623/17.15; 623/17.11; 623/17.13; 623/17.14; 623/17.16
(58) Field of Classification Search ... 623/17.11–17.16; 606/61, 246, 279
See application file for complete search history.

(56) References Cited

U.S. PATENT DOCUMENTS

| | | | |
|---|---|---|---|
| 5,989,294 A | 11/1999 | Marlow | |
| 6,176,882 B1 * | 1/2001 | Biedermann et al. | 623/17.15 |
| 6,533,791 B1 | 3/2003 | Betz et al. | |
| 6,610,093 B1 * | 8/2003 | Pisharodi | 623/17.15 |
| 7,273,496 B2 * | 9/2007 | Mitchell | 623/17.14 |
| 2002/0052656 A1 * | 5/2002 | Michelson | 623/17.11 |
| 2004/0143332 A1 * | 7/2004 | Krueger et al. | 623/17.14 |

FOREIGN PATENT DOCUMENTS

| | | |
|---|---|---|
| CA | 2 332 822 | 11/1999 |
| DE | 93 04 368.6 | 5/1993 |
| FR | 2 794 640 | 12/2000 |

* cited by examiner

*Primary Examiner*—Eduardo C Robert
*Assistant Examiner*—Andrew Yang
(74) *Attorney, Agent, or Firm*—Stroock & Stroock & Lavan LLP

(57) ABSTRACT

An intervertebral implant (1), including an upper section (10) provided with a ventral side area (11), a dorsal side area (12), two lateral side areas (13,14), a top apposition surface (15) and a bottom surface (16), a lower section (20) provided with a ventral side area (21), a dorsal side area (22), two lateral side areas (23,24), a bottom apposition surface (25) and a top surface (26), wherein the two sections (10,20) are moveable in relation to each other by means of two joints (38;39) arranged between the two sections (10;20), and wherein each of the joints (38;39) has a swivel axle (3;4) and the two swivel axles (3;4) are arranged perpendicular to each other, each of the joints (38;39) comprises at least one axle (34;36) coaxial to the relevant swivel axle (3;4) and a bearing shell (35;37) receiving the axle (34;36), and roll bodies (70) are inserted between the axles (34;36) and the bearing shells (35;37).

17 Claims, 4 Drawing Sheets

INTERVERTEBRAL IMPLANT WITH JOINT PARTS MOUNTED ON ROLLER BODIES

English translation of the International Patent Application No. PCT/CH02/00704 "Zwischenwirbelimplantat mit auf Wälzkörpern gelagerten Gelenkteilen"im Namber der Mathys Medizinaltechnik AG

BACKGROUND OF THE INVENTION

The invention relates to an intervertebral implant according to the generic term of Patent Claim 1 and to a process for the replacement of a defect, natural intervertebral disk by an intervertebral implant.

After removal of a damaged, natural intervertebral disk or a damaged nucleus pulposus of an intervertebral disk, implants or prostheses are inserted into the intervertebral space of two neighbouring vertebral bodies. This suggests the idea of restoring the situation as much as possible to a natural state, i.e. specifically to restore the original height of the intervertebral disk and thus the original distance between the two neighbouring vertebral bodies. Furthermore, the patient should be able to carry out movements of the neighbouring vertebral bodies relative to each other in the natural way, thereby incurring as little obstruction as possible. This essential feature of this system is its ability to retain the freedom of movement in forward/reverse inclination, i.e. flexion and extension of the vertebral bodies, and in lateral bending of the vertebral bodies within the natural limits. The natural sinews and muscles along the spinal column are in general left intact so that they further stabilise the movements of a mechanical intervertebral disk prosthesis A characteristic intervertebral disk endoprosthesis is state of the art from DE-A 35 29 761 BÜTTNER. This known intervertebral disk endoprosthesis basically consists of two symmetric closing plates with concave sliding surfaces facing each other, and each having an external surface for laying on the base plate, or the cover plate of the adjoining vertebral body, and a distance piece positioned between the closing plates with convex sliding surfaces arranged complementary to the concave sliding surfaces on the closing plates. The sliding surfaces are designed in one embodiment as section surfaces of a cylinder coat area, wherein the sliding surfaces arranged on the two closing plates are provided complementary to each of the adjoining sliding surfaces at the distance piece, and two complementary sliding surfaces form the articulation surfaces, which can be moved towards each other, of a joint element rotating around a swivel axle. The joint comprises an upper and a lower joint element, each of which has one swivel axle. The two swivel axles are set at 90° to each other. The disadvantages of this known intervertebral disk endoprosthesis is that a) the arrangement of an intervertebral disk endoprosthesis with only one fulcrum does not take sufficient account of the overlaying swivel movements transferred by the natural intervertebral disk, specifically in the case of anterior-posterior and in lateral flexion, which in the natural intervertebral disk are independent of each other;

b) the verterbral joint is put under strain by swivel movements, specifically with translation in the anterior-posterior direction (face joint), which could cause pain for the patient;

c) disadvantageous friction forces are generated by two articulating surfaces sliding on each other. This also leads to wear on the surfaces, including also abrasion and resistance in movement of the joint elements. There is also the risk of the "stick slip" effect;

d) a mechanical intervertebral disk prosthesis can scarcely prevent the further degeneration of the affected movement segments. Restoration of the original freedom of movement significantly reduces pain, with the resulting improvement to the patient's quality of life. A review of treatment will, however, have to be undertaken if pain recommences. This will normally involve complete removal of an intervertebral disk prosthesis of the standard model and a stiffening of the movement segment. This operation represents extreme discomfort and strain on the patient; and e) the form of contact areas to the neighbouring vertebral bodies is generally not taken into account. The conventional types of intervertebral disk prosthesis implants have flat contact areas, which are often supplemented with keel-type elevations.

BRIEF SUMMARY OF THE INVENTION

The invention is intended to remedy this situation. The invention is based on the task of creating an intervertebral implant that comprises a joint, the axles of which are provided with bearings with minimum friction.

The invention solves the task with an intervertebral implant that has the features of Claim 1 and with a process for replacing a defect, natural intervertebral disk by an intervertebral implant, comprising the steps.

The advantages achieved by the invention can generally be seen in that with the intervertebral implant according to the invention the swivel movements in anterior-posterior and lateral direction are independent of each other;

no translation movements of the vertebral bodies adjoining the implant are permitted, which relieves strain on the face joints;

the friction surface is reduced to a minimum by roll bodies rolling on surfaces; and the rolling movements of the roll bodies instead of the sliding movements of the articulation areas reduce the friction forces in the joint and as a result relative movement among the vertebral bodies, specifically lateral bending and flexion/extension movement of the spinal column is not impaired.

In a preferred embodiment of the intervertebral implant according to the invention, the, roll bodies are balls. Instead of balls, other rotation bodies can also be inserted, specifically the roll bodies used in conventional roller bearings, for example rolls, cones or tubs.

The number of roll bodies can measure between 3 to 12, preferably 4, for each joint. According to the size of the intervertebral implant, the diameter of the roll bodies, specifically the ball diameter will measure between 0.3 mm and 6 mm.

Due to the different positions of the natural swivel axles in the different intervertebral disk spaces along the spinal column the arrangement of the swivel axles can be warped or intersecting.

In another embodiment, the joint elements are designed in such a way that the central joint element coaxial to the swivel axle comprises at least one axle belonging to the lower joint and the lower joint element comprises at least one bearing shell receiving the axle, and the upper joint element coaxial to the swivel axle comprises at least one axle belonging to the upper joint, and the central joint element comprises at least one bearing shell receiving the axle. The configuration of the central joint elements with at least one axle on one of its surfaces and at least one bearing shell on the other of its surfaces allows the lowest possible design height of the intervertebral implant.

In a further embodiment of the intervertebral implant according to the invention, a means can be attached to the two sections from the ventral side areas which fixes the two sections ventral at a specific distance relative to each other. This measure provides the advantage that the two sections for insertion into the intervertebral space can be brought to a position with fixed height and can be moved around the joints after insertion into the intervertebral space and can be placed on the base or cover plate of the adjoining vertebral body.

In a further embodiment of the intervertebral implant according to the invention, the means allows temporary blocking of the mobility of the two sections around the joint. This measure provides the advantage that the joints integrated in the intervertebral space can be blocked by a minimum invasive operation. This is particularly advantageous in cases where the patient suffers from post-operative pain, i.e. where degeneration of the affected spinal column segment continues and the surgeon is considering a fusion of the affected vertebra. The means can preferably be attached to the two ventral side areas of the two sections. With this subsequent, secondary blocking of the mobility of the two sections around the joint, the intervertebral implant is stiffened and transferred to an arthrodesis implant (fusion cage).

In a further embodiment of the intervertebral implant according to the invention, the means comprises an insert, which can be placed into each depression on the surfaces of the upper and lower section opposite each other. These depressions are preferably provided as dovetail guides that are open on the ventral side areas, so that the ends of the insert arranged complementary to the dovetail guides can be inserted from ventral into the dovetail guides. This provides the advantage that the mobility of the two sections around the joints is blocked due to the positioning of the insert. The rigidity of the blocking can be increased when the dovetail guides are designed so that they are reduced is size towards the central axis of the intervertebral implant, which creates additional wedging of the insert in the dovetail guides.

In a further embodiment of the intervertebral implant according to the invention, the two sections are provided with drill holes for receiving the bone fixation means, specifically bone screws, wherein the drill holes are provided with longitudinal axes that stand perpendicular to the central axis. Preferably two drill holes will pass through one of the two sections from the ventral side area to the apposition surface. The longitudinal axes, if only an axial fixing of the intervertebral implant is provided, will then be able to stand only perpendicular to the central axis from a lateral perspective, or, if fixing of the intervertebral implant with stable angle is provided, will also from a lateral perspective diverge from the inner surfaces of the two sections against the apposition surfaces.

In a further embodiment of the intervertebral implant according to the invention, the drill holes for receiving the bone fixation means are provided with internal threads, which allows additional, rigid fixing of the bone fixation means in the two sections. The drill holes preferably have a conical shape so that a stronger fixing of the bone fixation means to each of the two sections can be achieved by the resulting conical thread connections between the internal threads and the external threads on the heads of the bone fixation means.

The apposition surfaces are preferably of convex shape and provided with a three-dimensional structure, preferably in the form of pyramid elevations. This arrangement of the apposition surfaces takes account of the anatomy of the vertebral body end plates.

The process according to the invention is intended primarily for replacing a defect, natural intervertebral disk by an intervertebral implant and comprises the following steps:
A) blocking of the joint(s) of an intervertebral implant by means of a special device placed in a certain position of the joint(s);
B) insertion of the intervertebral implant into the intervertebral space to be treated;
C) release and removal of the device inserted into the intervertebral implant for blocking the joint(s). Blocking the joint provides the advantage that the moveable sections with the external apposition surfaces can be inserted more easily into the intervertebral space to be treated.

In a further application of the process according to the invention, this comprises the subsequent blocking of the joint (s) on the implanted intervertebral implant by means of the device intended for blocking the joint(s). This provides the advantage that if the patient should suffer from post-operative pains or in case of a further degeneration of the movement segment, the joint(s) on the intervertebral implant are blocked post-operative by the insertion of the means intended for this purpose. This subsequent blocking can be achieved with an minimally invasive, preferably a laprascopic operation. The intervertebral implant then assumes the function of a cage, so that the affected movement segment of the spinal column can be stiffened.

BRIEF DESCRIPTION OF THE DRAWINGS

The invention and refinements of the invention are described in more detail below on the basis of a partially schematic illustration of several embodiments.

DETAILED DESCRIPTION OF THE INVENTION

Figure 1:
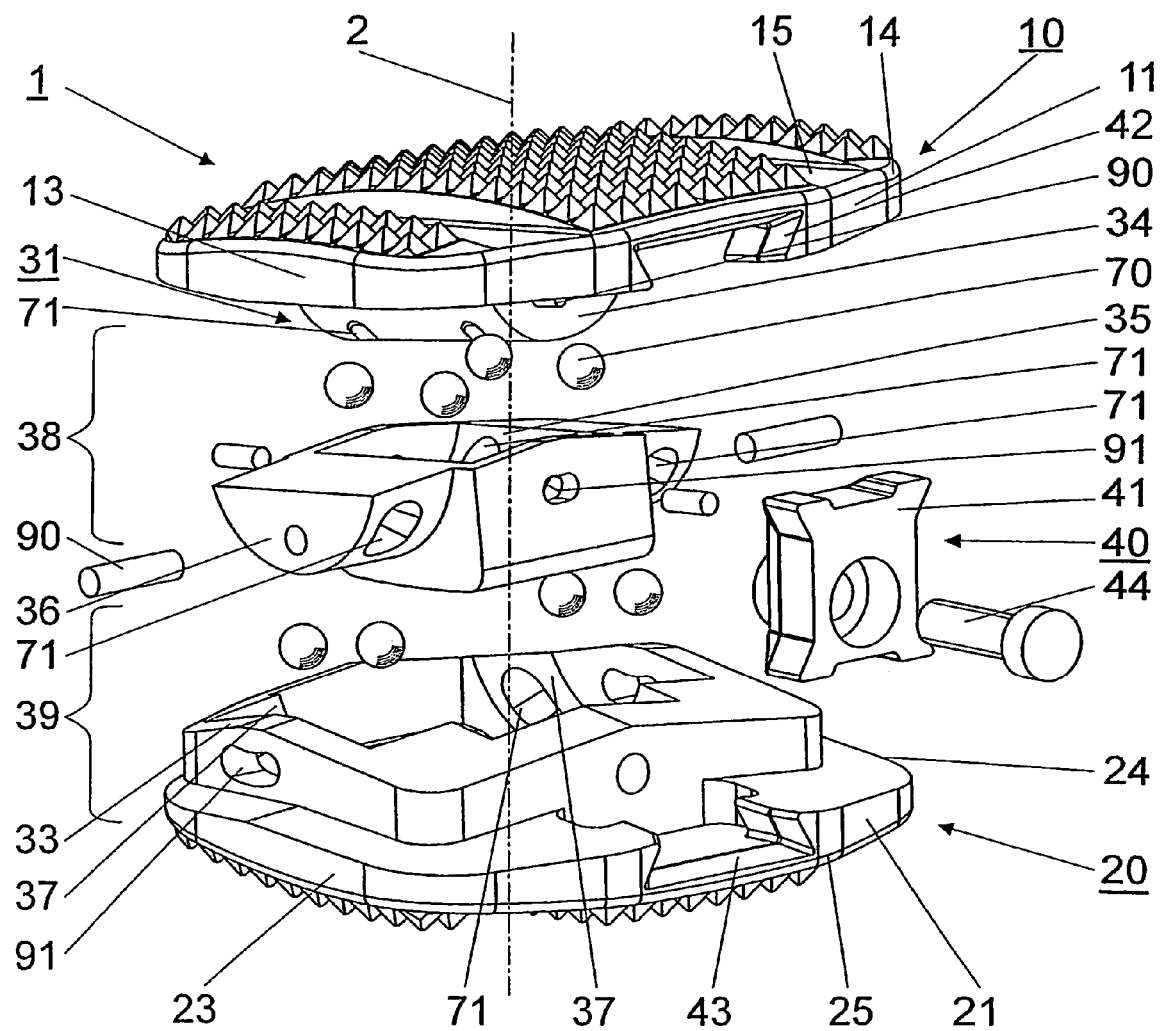
FIG. 1 shows an explosion diagram of one embodiment of the intervertebral implant according to the invention.
Figure 2:
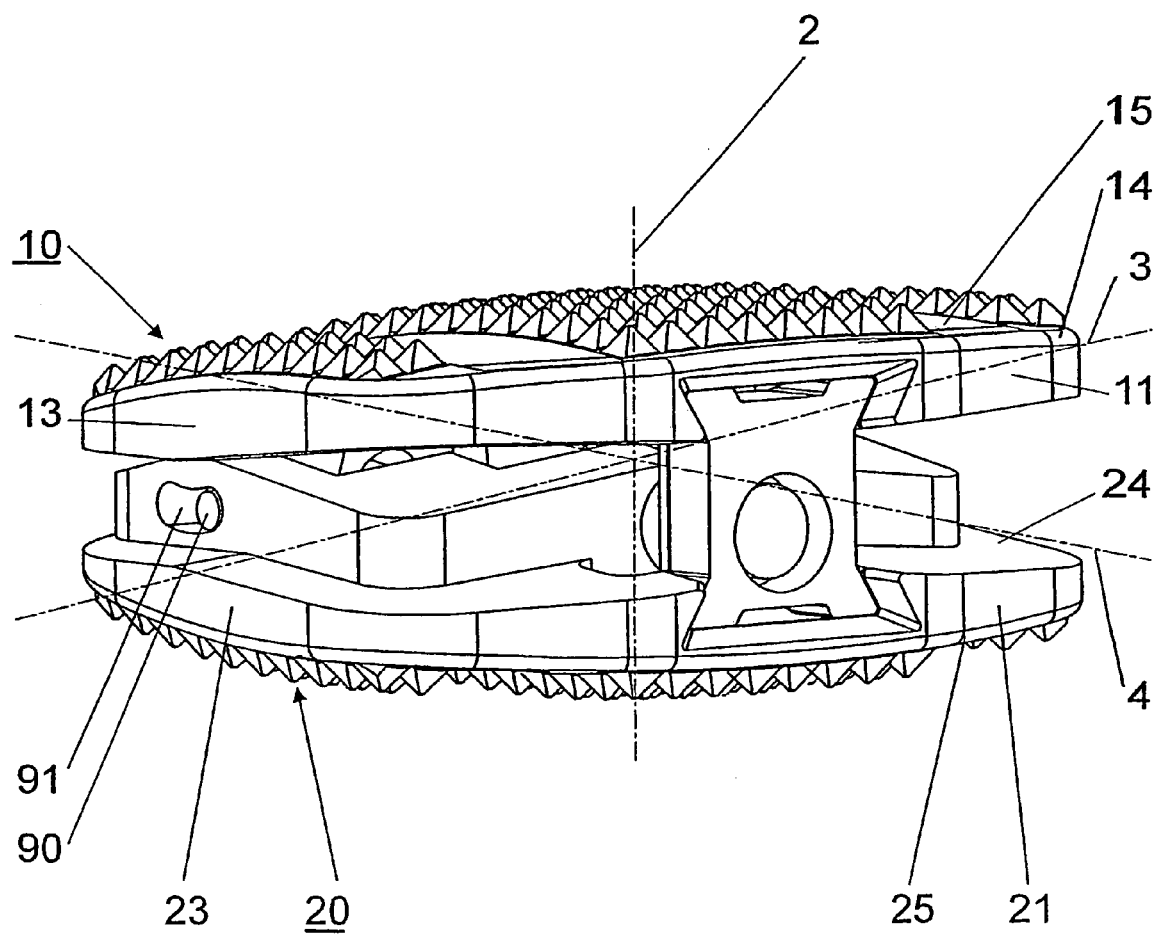
FIG. 2 shows a perspective view of the embodiment of the intervertebral implant according to the invention shown in FIG. 1 in assembled state.

FIG. 1 and FIG. 2 show an embodiment of the intervertebral implant 1 according to the invention, which comprises an upper section 10 with a top apposition surface 15 arranged perpendicular to the central axis 2 for laying on the base plate of an adjoining vertebral body, a lower section 20 with a lower apposition surface 25 arranged perpendicular to the central axis 2 for laying on the cover plate of the adjoining vertebral body and two joints 38;39. The upper section 10 and the lower section 20 are connected with the joints 38;39 and moveable in relation to each other, whereby the mobility of the upper section 10 relative to the lower section 20 is restricted by a first swivel axle 3 arranged perpendicular to the central axis 2 within an angle range of +10° to −6° and by a second swivel axle 4 arranged perpendicular to the central axis 2 and vertical to the first swivel axle 3 within an angle range of ±7°.

The two joints 38;39 are realised by three joint elements 31;32;33, of which the lower joint element 33 and the upper joint element 31 each form a joint 38;39 interacting with the central joint element 32. The joints 38;39 are each provided with a swivel axle 3;4, wherein the swivel axles stand vertical to each other and vertical to the central axis 2. The lower joint 39 comprises a two-part axle 36 arranged on the central joint element 32 and coaxial to the first swivel axle 3, and two bearing shells 37 arranged on the lower joint element 33 to receive the axle 36. The upper joint 38 is made up of an axle 34 arranged on the upper joint element 31 an coaxial to the second swivel axle 4 and a bearing shell 35 arranged on the central joint element 32 and receiving the axle 34. The bearing shells 35;37 and the axles 34;36 are provided with grooves 71 that are arranged as circular arc in a cross section to the swivel axle 3;4 seen from an orthogonal perspective to the relevant swivel axle 3;4 and which serve to receive balls as roll bodies 70.

In addition, coaxial cams 90 are also attached to the axles 34;36 terminal to the swivel axles 3;4, which are fitted with sliding action in oblong hole guides 91 in the lower joint element and in the central joint element 32. Because of the cams 90 moving in the oblong hole guides 91, the swivel angles of the joint elements 31;32;33 around the swivel axles 3;4 are limited. In addition, the intervertebral implant 1 is held together by the cams 90 positioned in the oblong hole guides 91.

The mobility of the two sections 10;20 relative to each other can be blocked by the means 40 in a way that allows release. The means 40 comprises in the embodiment described here an insert 41 that can be slid in from the ventral side areas 11;21 of the two sections 10;20 perpendicular to the central axis 2 and parallel to the lateral side areas 13;14;23;24 of the two sections 10;20. The insert 41 is slid in two depressions 42;43, provided in the form of dovetail guides. The insert 41 is inserted from the ventral side areas 11;21 of the two sections 10;20 into the depressions 42;43 composed as dovetail guides and fitted to the lower section 20 by means of a screw 44. The insert 41 is furthermore arranged in the terminal state complementary to the depressions 42;43, so that the two sections 10;20 with fitted insert 41 are fixed relative to each other parallel to the central axis 2.

Figure 3:
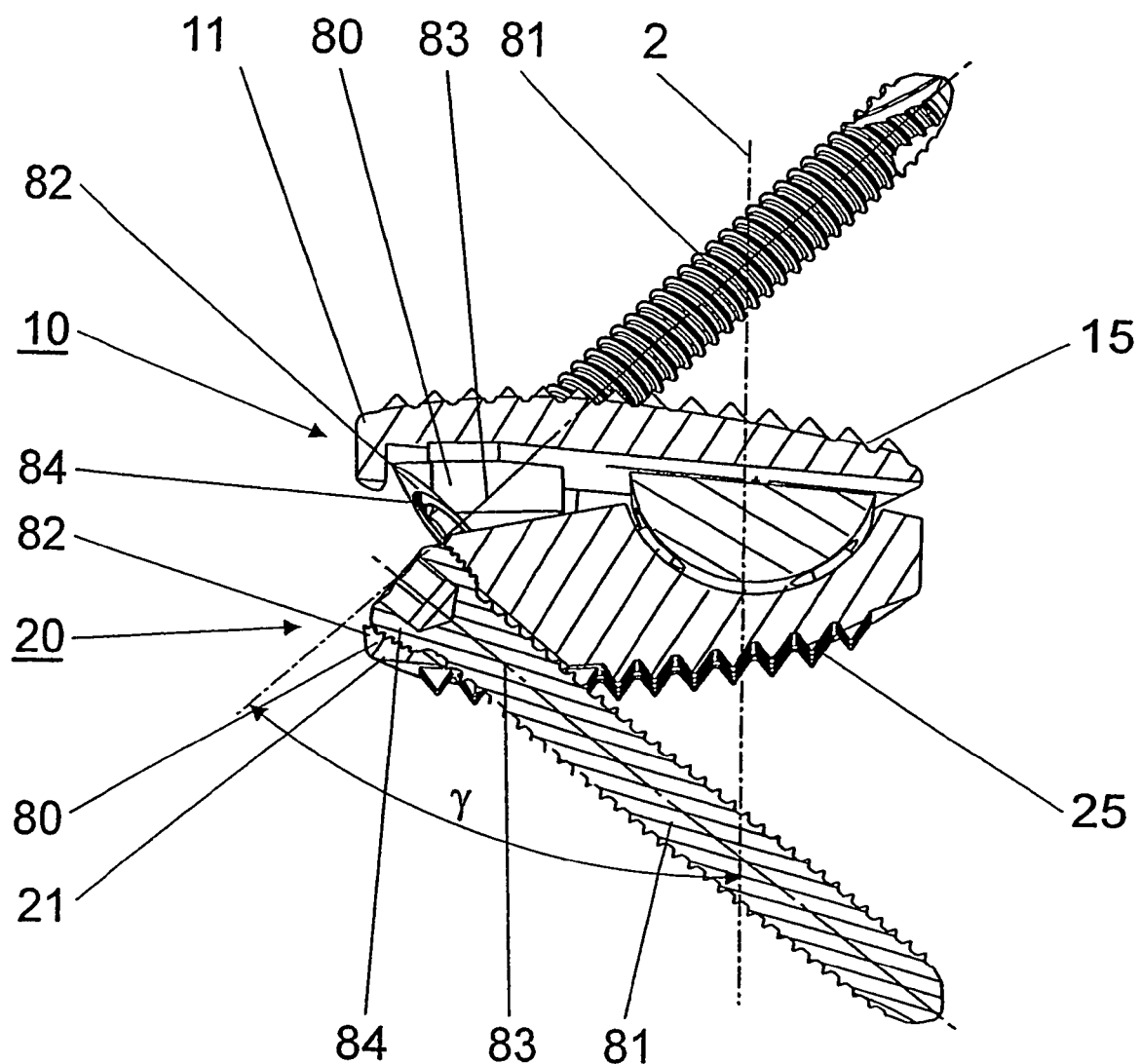
FIG. 3 shows a lateral view of a further embodiment of the intervertebral implant according to the invention.

FIG. 3 illustrates an embodiment of the intervertebral implant 1 according to the invention, which differs from the embodiment illustrated in FIG. 1 and FIG. 2 only in that the two sections 10;20 also comprise drill holes 80 for receiving the bone fixation means 81, whereby the bone fixation means 80 is provided in this case as bone screws. The drill holes 80 are provided with longitudinal axes 83 that form an angle γ with the central axis 2. In addition, each two drill holes 80 (FIG. 4) run trough one of the two sections 10;20 from the ventral side area 11;21 to the apposition surface 15;25. The longitudinal axes 83 of the drill holes 80 are standing perpendicular to the central axis 2 from only a lateral perspective. The drill holes 80 are furthermore provided in conical design and tapering towards the apposition surfaces 15;25 and provided with internal threads 82 that are used for screwing reception of the screw heads 84 of the bone fixation device 81 realised here in the form of bone screws and provided with complementary external threads.

Figure 4:
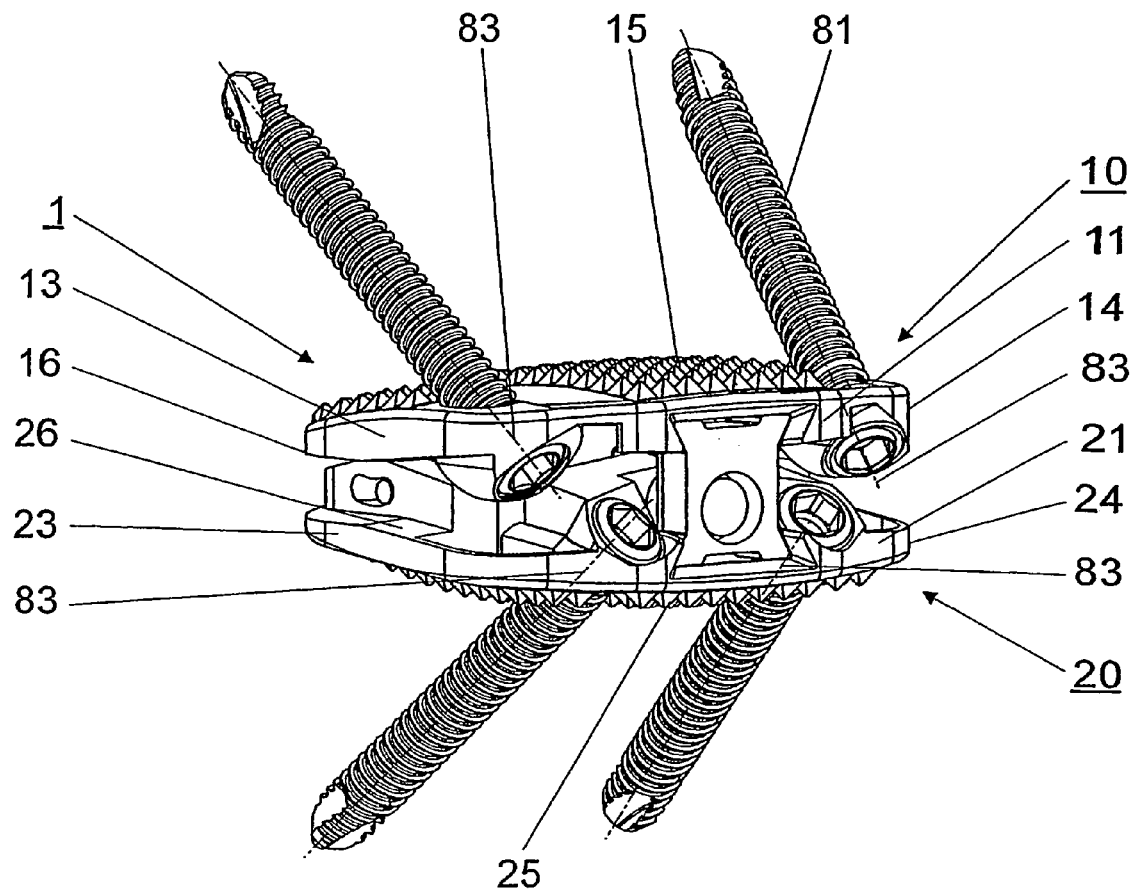
FIG. 4 shows a perspective view of the embodiment according to FIG. 3.

The embodiment of the intervertebral implant 1 according to the invention illustrated in FIG. 4 differs from the embodiment illustrated in FIG. 3 only in that the longitudinal axes 83 of the drill holes 80 also diverge from the ventral perspective from the inner surfaces 16;26 of the two sections 10;20 against the apposition surfaces 15;25.

The invention claimed is:

1. An intervertebral implant sized and configured for implantation between an upper and lower vertebra, the implant comprising:

an upper member having an upper surface for contacting at least a portion of the upper vertebra, a bottom surface, a dorsal side surface, a ventral side surface, and a pair of lateral side surfaces;

a lower member having a lower surface for contacting at least a portion of the lower vertebra, a top surface, a dorsal side surface, a ventral side surface, and a pair of lateral side surfaces; and a central joint element having a top surface, a bottom surface, a dorsal side surface, a ventral side surface, and a pair of lateral side surfaces;

wherein the bottom surface of the upper member is operatively coupled to the top surface of the central joint element so that the upper member is moveable with respect to the central joint element about a first swivel axis, and the top surface of the bottom member is operatively coupled to the bottom surface of the central joint element so that the bottom member is moveable with respect to the central joint element about a second swivel axis, the first swivel axis being substantially perpendicular to the second swivel axis; and wherein at least one of the side surfaces of at least one of the upper and lower members includes at least one elongated hole, the at least one elongated hole receiving a cam operatively associated with the central joint element, the interaction of the cam and the at least one elongated hole controlling the amount of movement between the central joint element and at least one of the upper and lower members.

2. The intervertebral implant according to claim 1, wherein at least one of the bottom surface of the upper member and the top surface of the central joint element includes an elongated projection and the other one of the bottom surface of the upper member and the top surface of the central joint element includes an elongated recess for receiving the elongated projection; and wherein at least one of the top surface of the lower member and the bottom surface of the central joint element includes an elongated projection and the other one of the top surface of the bottom member and the bottom surface of the central joint element includes an elongated recess for receiving the elongated projection.

3. The intervertebral implant according to claim 2, further comprising one or more roll bodies between the corresponding projection and recess formed on the upper member and the central joint element and between the corresponding projection and recess formed on the lower member and the central joint element.

4. The intervertebral implant according to claim 3, wherein the roll bodies are rotation-symmetric bodies sized and configured to be received in one or more grooves formed in the corresponding projections and recesses.

5. The intervertebral implant according to claim 3, wherein the roll bodies are rotation-symmetric bodies.

6. The intervertebral implant according to claim 3, wherein the corresponding projection and recess formed on the upper member and the central joint element and the corresponding projection and recess formed on the lower member and the central joint element include a plurality of grooves for partially receiving the roll bodies.

7. The intervertebral implant according to claim 3, wherein the corresponding projection and recess formed on the upper member and the central joint element and corresponding projection and reccess formed on the lower member and the central joint element include a plurality of grooves in which the roll bodies are conduced in axial direction.

8. The intervertebral implant according to claim 1, wherein at least one of the side surfaces of the upper member includes a depression for receiving at least a portion of an insert member, and one of the side surfaces of the lower member includes a depression for receiving at least another portion of the insert member, the insert member being threadably coupled to one of the upper and lower sections so the position of the upper section can be temporary fixed with respect to the lower section 9. The intervertebral implant according to claim 8, wherein the depressions are formed on the ventral side surfaces of the upper and lower members.

10. The intervertebral implant according to claim 9, wherein the insert member includes first and second ends, the depressions formed on the ventral side surfaces of the upper and lower members are dovetail guides and the first and second ends of the insert are arranged complementary to these dovetail guides.

11. The intervertebral implant according to claim 10, wherein the dovetail guides are tapered from the ventral side surfaces towards the dorsal side surfaces.

12. The intervertebral implant according to claim 1, wherein the upper member includes at least two holes extending from the ventral side surface to the top surface thereof for receiving bone fixation devices, and the lower member includes at least two holes extending from the ventral side surface to the lower surface thereof for receiving fixation devices, and wherein the implant has a central axis and the bone fixation devices each have a longitudinal axes, the longitudinal axis of the bone fixation devices diverging from the central axis of the implant.

13. The intervertebral implant according to claim 1, wherein the upper and the lower members each comprises at least two drill holes running through from the ventral side surfaces to the top surfaces with longitudinal axes for receiving bone fixation devices.

14. The intervertebral implant according to claim 13, wherein the longitudinal axes of the drill holes make an angle gamma with a central axis of the implant, the angle gamma lies in a range between 20 degrees and 65 degrees.

15. The intervertebral implant according to claim 13, wherein the longitudinal axes of the drill holes as seen from the ventral side surfaces diverge from the inner surfaces against the top surfaces.

16. The intervertebral implant according to claim 13, wherein the drill holes are conically tapered towards the top surfaces.

17. The intervertebral implant according to claim 13, wherein the drill holes have an internal thread.

\* \* \* \* \*